United States Patent [19]

D'Amico

[11] Patent Number: 5,222,947
[45] Date of Patent: Jun. 29, 1993

[54] SELF RECAPPING INJECTION NEEDLE ASSEMBLY

[76] Inventor: Elio D'Amico, 1358 Ashley La., Addison, Ill. 60101

[21] Appl. No.: 694,549

[22] Filed: May 2, 1991

Related U.S. Application Data

[63] Continuation-in-part of Ser. No. 510,627, Apr. 18, 1990, abandoned.
[51] Int. Cl.⁵ .............................................. A61M 5/32
[52] U.S. Cl. .................................... 604/198; 604/263
[58] Field of Search ............... 604/198, 187, 263, 110, 604/111, 192

[56] References Cited

U.S. PATENT DOCUMENTS 4,923,447  5/1990  Morgan ............................... 604/198
4,929,232  5/1990  Sweeney et al. ..................... 604/111
4,929,237  5/1990  Medway ............................... 604/198

Primary Examiner—John D. Yasko

[57] ABSTRACT

Generally there is provided an improved cover for an injection needle assembly which is slidably engaged to a hub and urged toward its protective position by a spring. This hub and the sleeve cover present a radius larger than the barrel of the syringe, and a needle mounted within the hub is protected by the sleeve cover. When the needle assembly is mounted to the syringe barrel, the sleeve cover is shifted rearwardly to expose the needle and it is held there by a pin/groove lock. After use the sleeve cover is rotated to release the lock and the cover shifts back to its original protective position.

4 Claims, 5 Drawing Sheets

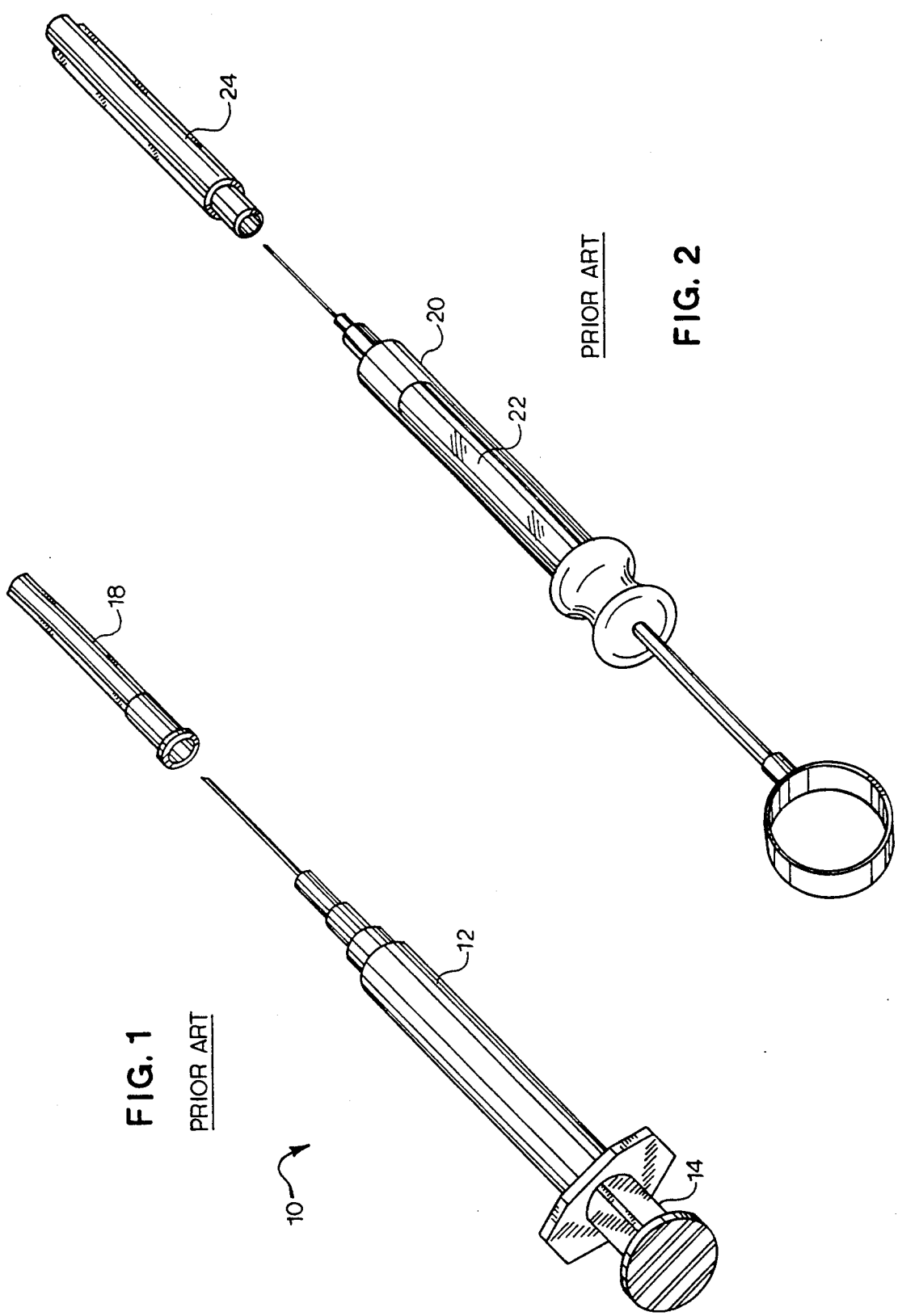

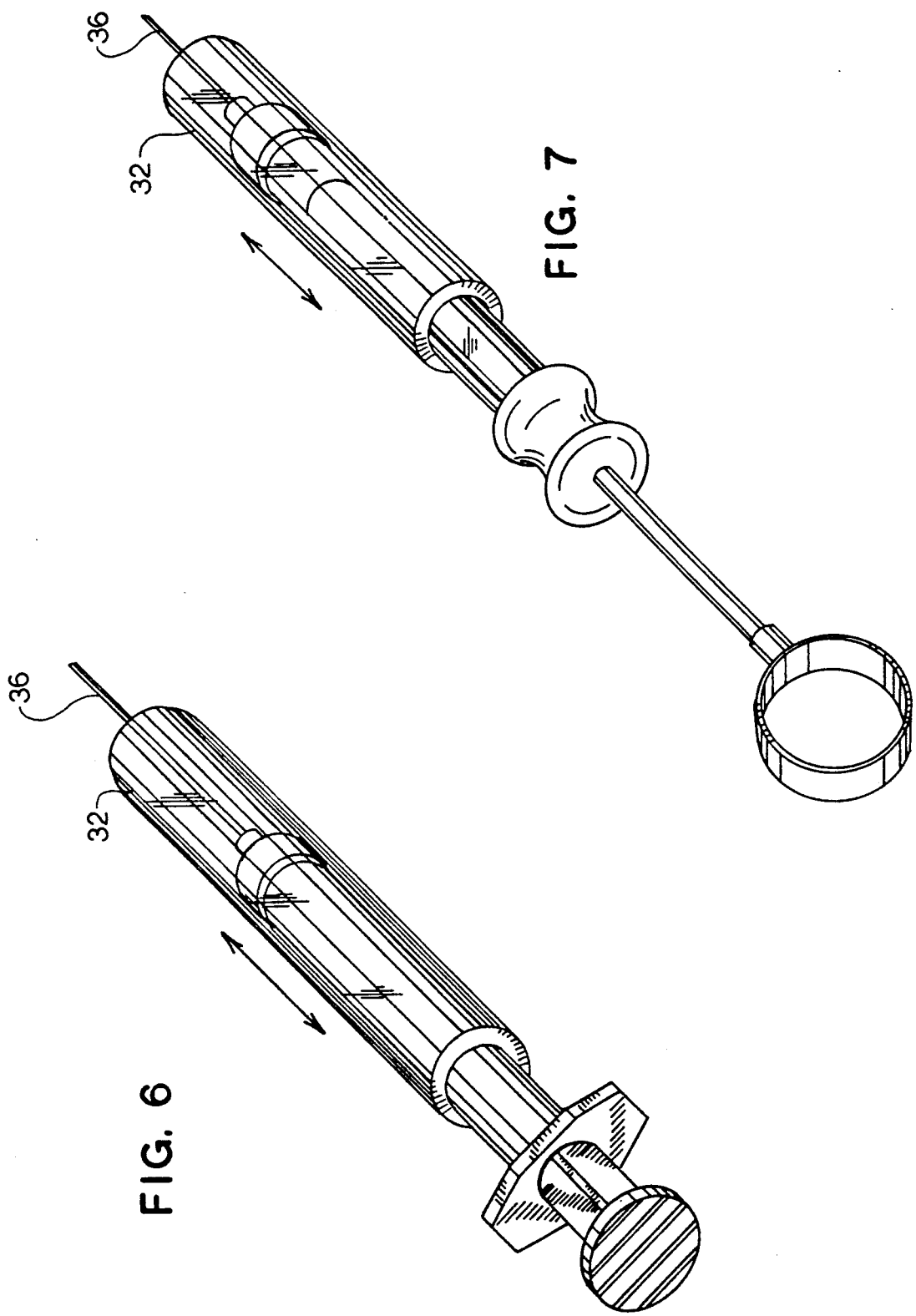

SELF RECAPPING INJECTION NEEDLE ASSEMBLY

This is a continuation-in-part of application Ser. No. 07/510,627 filed Apr. 18, 1990 now abandoned.

BACKGROUND OF THE INVENTION

1. Field of the Invention

The present invention relates generally to needle assemblies used for injection of medication or withdrawal of blood or fluid samples. This invention further relates to an improvement which protects the needle when not in use to prevent unintentional contact with the needle, and more particularly relates to a new self recapping feature.

2. Description of the Prior Art

Previously, injection needle assemblies have employed simply a removable plastic cover. As shown in the prior art illustrated in FIGS. 1 and 2, these covers fit over the needle portion and frictionally engage the assembly. After use, the cover may be replaced to guard the needle; but such recapping in itself is dangerous and may result in unintentional contact with the point.

SUMMARY OF THE INVENTION

Generally there is provided herein a design for an improved sleeve cover for a needle which is slidably engaged to a hub within the needle assembly. This hub and the sleeve cover present a radius larger than the barrel of the syringe, and the needle is mounted within the hub. When the assembly is mounted to the barrel of the syringe, the sleeve cover can be shifted to expose the needle by sliding it rearwardly over the hub. After use, the sleeve cover is moved back to its original protective position to recap the needle. In a further feature of the invention, a spring bias is provided to urge the sleeve cover forwardly to the protective position and a thumb actuated lock is provided to facilitate the recapping.

BRIEF DESCRIPTION OF THE DRAWINGS

FIG. 1 is a perspective view of a needle assembly and cover of the prior art.

FIG. 2 is a perspective view of a second needle assembly and cover of the prior art.

FIG. 6 illustrates one embodiment of the needle assembly of the prior art incorporating the sliding cover improvement of one aspect of the present invention.

FIG. 7 illustrates a second embodiment of the needle assembly of the prior art incorporating the sliding cover improvement of one aspect of the present invention.

Figure 3:
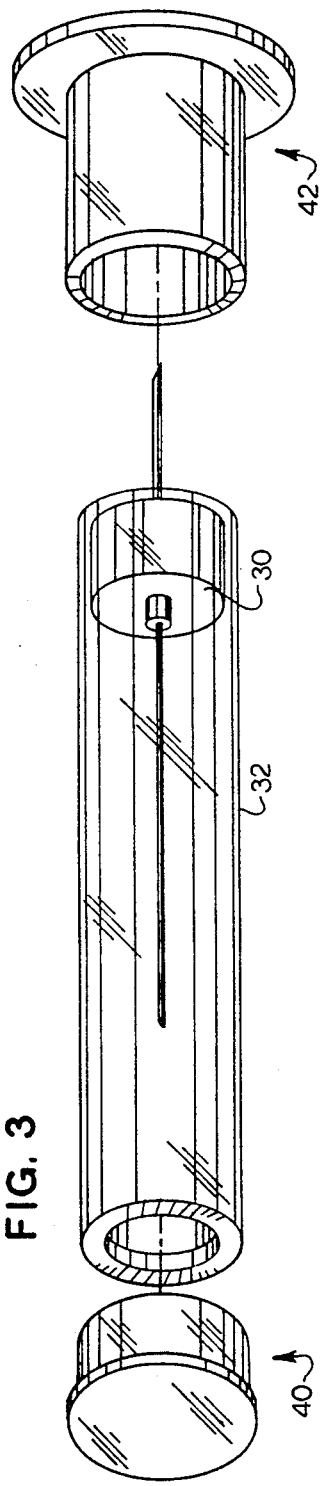
FIG. 3 is a perspective view of a needle attachment for incorporation into a needle assembly in accordance with one aspect of the present invention.

While the invention will be described in connection with a preferred embodiment and particular design of needle assemblies, it will be understood that I do not intend to limit the invention to that embodiment. On the contrary, I intend to cover all alternatives, modifications, and equivalents as may be included within the spirit and scope of the invention as applied to the various known syringe and needle assemblies as defined by the appended claims.

DESCRIPTION OF THE PREFERRED EMBODIMENT

Turning first to the prior art shown in FIGS. 1 and 2, there is depicted two versions of injection or hypodermic needle apparatus currently in use. In the first (FIG. 1) the apparatus consists of a syringe portion 10 having a barrel reservoir portion 12. A piston 14 reciprocates within the barrel to draw fluid into the reservoir or to eject fluid therefrom. In some instances the syringe is dispensed with the needle attached, as shown in FIG. 1. In a variation, the needle portion may be dispensed separately; and the needle portion is attached to the syringe by friction or screw means. In either case, the cover 18 is provided as a cap over the needle and is removed prior to use. It may then be replaced after use in an attempt to protect against accidental contact with the needle. Unfortunately, this recapping all too frequently results in inadvertent contact with the needle.

A similar situation is presented with the injection needle apparatus depicted in FIG. 2. In this version the syringe barrel 20 is designed to accept an ampoule 22 and to eject the fluid therefrom. A separately dispensed needle assembly is attached by screw means to the barrel and the needle extends into the ampoule. The needle cover 24 is removed to reveal the needle and, as before, the cover is replaceable after use. In either instance the sliding cover improvement described herein may be incorporated to initially reveal and to later recap the needle. Moreover, by use of the self recapping technique described below, protection is greatly enhanced.

Figure 4:
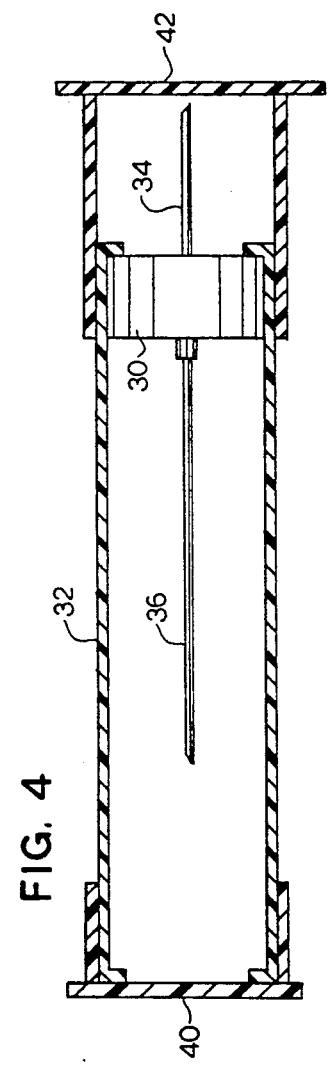
FIG. 4 is a sectional view of the attachment of FIG. 3.
Figure 5:
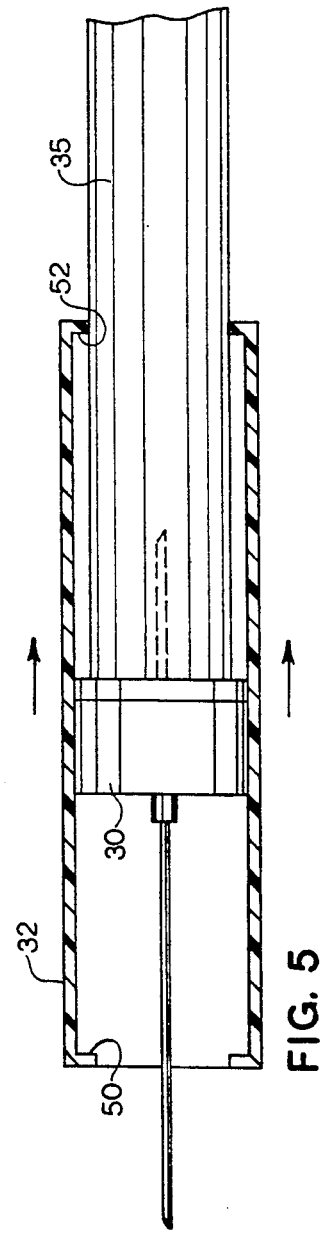
FIG. 5 is an illustration in cross section of the sliding cover recapping concept of one aspect of the present invention.
Figure 8:
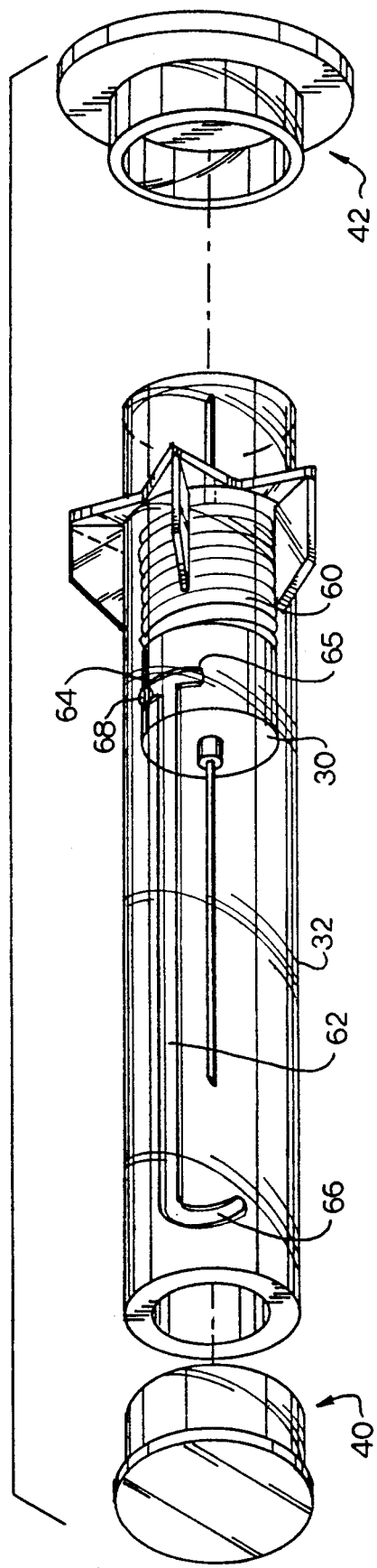
FIG. 8 is a perspective view of a needle assembly in accordance with a second aspect (self recapping) of the present invention.
Figure 12:
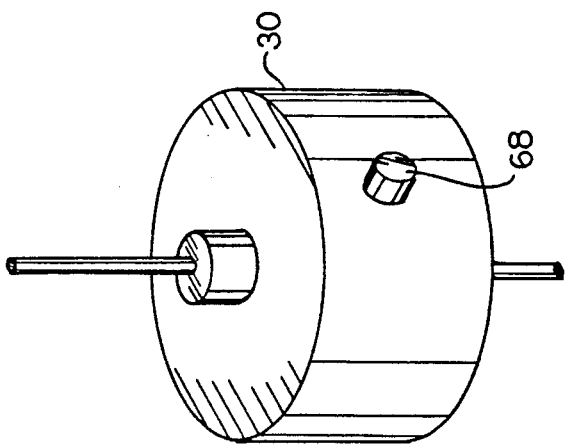
FIG. 12 is a perspective view of the hub of the assembly of FIG. 11.
Figure 9:
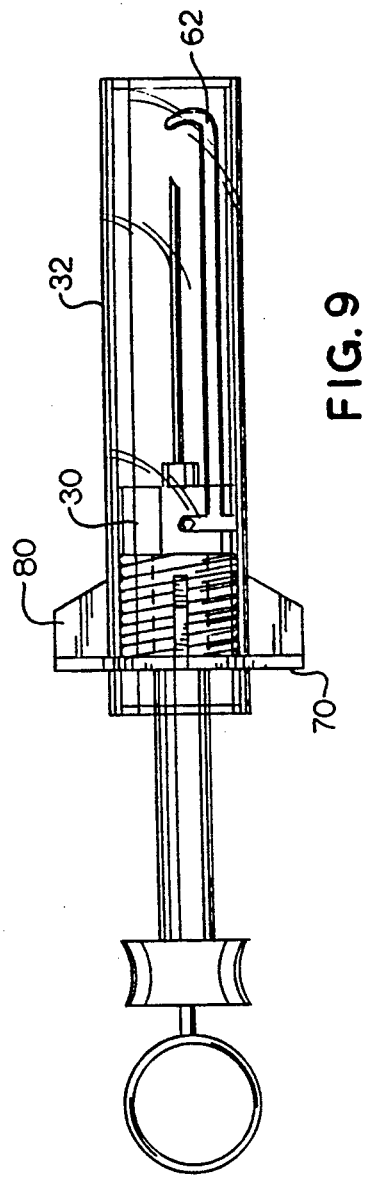
FIG. 9 is a sectional view of the needle assembly of FIG. 8 attached to a prior art syringe.

In an example of the sliding cover aspect of the present invention, there is shown in FIGS. 3-5 a needle attachment consisting of a hub 30 and a sliding sleeve cover 32. The needle is mounted within the hub (in accordance with prior art techniques) and projects a rear portion 34 to engage the reservoir 35 (or ampoule) of the syringe and a forward portion 36 to penetrate a patient's skin for injection. The radius of the hub, and therefore the inside diameter of the sleeve cover, are greater than that of the barrel reservoir, and this allows the barrel to telescope into the sleeve cover.

A cap 40 seals the forward portion of the sleeve and is removed prior to use. When the needle attachment is dispensed independent of the syringe, a rear cap 42 is provided to seal the rear portion of the sleeve. Removal of the rear cap allows attachment of the needle to the syringe in accordance with well known friction or screw means. Typically the hub forms a receptacle to accept a fitting provided on the syringe barrel, and this receptacle operates to secure the hub to the syringe.

When the needle assembly is attached, the rear portion 34 of the needle extends through the fitting to access the reservoir within the barrel of the syringe. Once the needle assembly is secured to the barrel, since the internal diameter of the sleeve cover is larger than the outside diameter of the barrel reservoir, the sleeve may now be shifted rearwardly (FIG. 5) to expose the forward portion of the needle. To facilitate this movement, the hub and the internal surface of the sleeve cover are smooth and form a sliding fit. An inwardly projecting annular lip 50 is provided on the forward end of the sleeve cover and an annular lip 52 is provided on the rear extremity of the sleeve cover. These lips catch on the peripheral edge of the hub member when the sleeve cover has been shifted fully to its forward or rearward position. After use, the sleeve may be easily shifted back to its original position, shielding the needle; and the forward cap can then be safely replaced if desired. If the needle and cover assembly is removed from the barrel, the rear cap can also be replaced.

Sliding movement of the cover is semi-automatic in a further feature of the invention. This accomplishes an instant self recapping and is achieved by providing a spring bias in the form of a coil spring 60 (FIGS. 8–11) which acts to force the cover toward its protective position. The position of the cover is further controlled by a longitudinally aligned groove 62 having transverse legs 64, 65 and 66 defined at its extremities. A pin 68 protruding from the hub 30 travels within the groove; and when positioned within one of the transverse legs, the pin secures the cover against movement until manually unlocked.

To maintain the cover in its normal protective position, the coil spring 60 is fastened to the rear face of the hub 30 and the flange 70 at the rear of the cover. The unsprung condition of the spring is the compressed state and it resists extension. Consequently, the spring pulls the rear of the cover towards the hub to maintain the cover 32 in the protective position. The cover is locked in this protective position by a slight rotation of the cover to position the pin 68 within transverse leg 64 of the groove. The ends of the assembly are sealed with forward and rear caps 40 and 42, as before, to protect the assembly during transport and handling.

To use the needle assembly, the end seals are removed and the hub screwed onto the selected syringe. Due to the clockwise twist during syringe attachment, the pin 68 remains positioned in transverse leg 64. The professional may then counter rotate the cover slightly to position the pin in the longitudinal groove. In this position the cover may then be shifted longitudinally to expose the needle, extending and tensioning the coil spring, and then twisted further counter clockwise to position the pin within the arcuate extremity leg 66. Under tension from the spring, the pin is held at the end of the arcuate leg until released.

Figure 10:
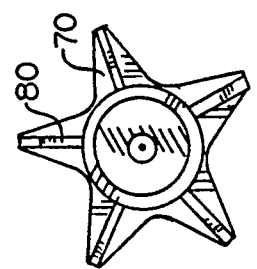
FIG. 10 is an end view of the needle assembly of FIG. 8.
Figure 11:
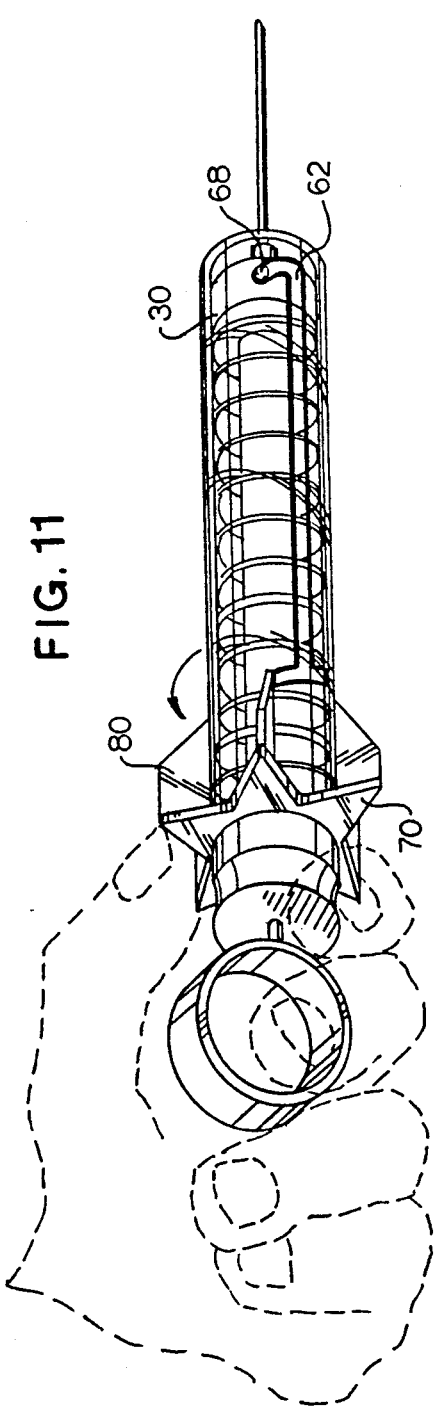
FIG. 11 is a perspective view of the self recapping needle assembly illustrating the thumb release feature.

As shown in FIG. 10, the rear portion of the cover exhibits fins 80 spaced around the cover and rigidly supported by a flange 70. Turning to FIG. 11, it can be seen that thumb pressure applied to one of the fins 80 causes the cover to rotate. This positions the pin 68 within the longitudinal groove, and automatically under spring tension the cover now snaps back to its protective position, safely recapping the needle. The needle assembly may now be safely resealed for disposal.

From the foregoing description, it will be apparent that modifications can be made to the apparatus and method for using same without departing from the teachings of the present invention. Accordingly, the scope of the invention is only to be limited as necessitated by the accompanying claims.

I claim:
1. In an injection needle assembly having a barrel reservoir portion, a protruding needle affixed to the barrel portion, and means for filling or emptying the reservoir through the needle, the improvement comprising:
   a hub defined about the needle proximate the conjunction of the needle with the barrel portion, said hub presenting an outside diameter larger than the portion;
   a sleeve cover slidably engaged to said hub and selectively movable between a first and second position, said sleeve cover being arranged to extend over the needle when in said first position and to expose the needle and extend over the barrel when in said second position;
   means for urging said sleeve cover towards said first position;
   means for releasably locking said sleeve cover in said second position comprising a longitudinal groove defined in said sleeve cover, and a pin positioned to protrude from said hub and to engage said groove, said groove further comprising transverse legs to secure said sleeve cover position relative to said hub; and
   means for releasing said sleeve cover from said second position to allow return of said sleeve cover to said first position comprising fin means spaced about the outer periphery of the rear portion of said sleeve cover for causing selective rotation of said sleeve cover in response to pressure applied thereto.

2. The injection needle assembly of claim 1 further comprising front and rear cap means for closing the extremities of said sleeve.

3. An improved needle attachment device for an injection needle assembly having a barrel reservoir portion adapted to receive the needle attachment and means for filling or emptying the reservoir through the needle, comprising:
   a hub member having an outside diameter larger than the barrel portion;
   an injection needle mounted within said hub member;
   a sleeve cover slidably engaged to said hub and selectively movable between a first and second position, said sleeve cover being arranged to extend over the needle when in said first position and to expose the needle and extend over the barrel when in said second position;
   means for urging said sleeve cover towards said first position;
   means for releasably locking said sleeve cover in said second position comprising a longitudinal groove defined in said sleeve cover and a pin positioned to protrude from said hub and to engage said groove, said groove further comprising transverse legs to secure the sleeve cover position relative to said hub; and
   means for releasing said sleeve cover from said second position to allow return to said first position comprising fin means spaced about the outer periphery of the rear portion of said sleeve cover for causing selective rotation of said sleeve cover in response to pressure applied thereto.

4. The injection needle assembly of claim 3 further comprising front and rear cap means for closing the extremities of said sleeve.

* * * * *